(12) United States Patent
Burton (10) Patent No.: US 8,697,128 B2
(45) Date of Patent: Apr. 15, 2014

(54) CARBIDE-DERIVED-CARBON-BASED OXYGEN CARRIERS

(75) Inventor: Robert A. Burton, Columbia, MD (US)

(73) Assignee: BAE Systems Information and Electronic Sytems Integration Inc., Nashua, NH (US)

( * ) Notice: Subject to any disclaimer, the term of this patent is extended or adjusted under 35 U.S.C. 154(b) by 574 days.

(21) Appl. No.: 12/641,507

(22) Filed: Dec. 18, 2009

(65) Prior Publication Data

US 2011/0151007 A1  Jun. 23, 2011

(51) Int. Cl.
*A61K 9/14* (2006.01)

(52) U.S. Cl.
USPC ............................ 424/489; 424/400; 514/13.4

(58) Field of Classification Search
None
See application file for complete search history.

(56) References Cited

U.S. PATENT DOCUMENTS

| | | | |
|---|---|---|---|
| 4,743,545 A * | 5/1988 | Torobin | 435/41 |
| 5,234,903 A * | 8/1993 | Nho et al. | 514/13.4 |
| 2009/0036302 A1 * | 2/2009 | Gogotsi et al. | 502/402 |

OTHER PUBLICATIONS

Gemeinhart RA, J Chen, H Park, and K Park. 2000. pH-sensitivity of fast responsive superporous hydrogels. J Biomater Sci Polym Ed.; 11(12): abstract.*
Nemoto M et al. 2006. Salvage of focal cerebral ischemic damage by transfusion of high O2-affinity recombinant hemoglobin polymers in mouse. J. Appl. Physiol.; 100: 1688-1691.*

* cited by examiner

*Primary Examiner* — Brian-Yong Kwon
*Assistant Examiner* — David Browe
(74) *Attorney, Agent, or Firm* — Rossi, Kimms & McDowell; Marc A. Rossi (57) ABSTRACT

An oxygen delivery system is disclosed. The basis of the oxygen deliver system is a carbide-derived carbon (CDC). The CDC can be tuned to carry $O_2$ directly (CDC OC), or hemoglobin can be adsorbed to provide a hemoglobin-based oxygen carrier (CDC HBOC). The delivery system allows the use of a variety of hemoglobins which differ in their oxygen dissociation profiles, including variant and mutant hemoglobins from other species. The delivery system is biocompatible and stable, and is able to irreversibly bind and hold large amounts of functional hemoglobin variants. The CDC HBOC and CDC OC provide a safe and effective blood substitute for combat casualty care, as well as being useful for oxygen delivery in other contexts.

24 Claims, 1 Drawing Sheet

CARBIDE-DERIVED-CARBON-BASED OXYGEN CARRIERS

BACKGROUND OF THE INVENTION

A. Field of the Invention

The present invention relates generally to blood substitutes and, more particularly, to a carbide-derived-carbon hemoglobin-based oxygen carrier (CDC HBOC) and a carbide-derived-carbon oxygen carrier (CDC OC).

B. Description of the Related Art

Blood loss is the primary cause of preventable civilian trauma related death (Hoyt et al., 1994; Sauaia et al., 1995), with trauma being the leading cause of death for ages 1-34 (Bonnie et al., 1999; Holcomb, 2004). Approximately 80% of trauma related civilian deaths and combat casualty fatalities result not from the initial injury but the associated exsanguination and hemorrhagic shock (Hoyt et al., 1994; Bellamy, 1984; Champion et al., 2003). A decrease in oxygenation capacity as a result of blood loss, in addition to hypovolemia, contributes to the observed high mortality rates (Muir, 2006).

The transfusion of whole blood or packed red blood cells (pRBCs) requires that blood be type matched and free of pathogens such as HIV and hepatitis. At the same time, RBCs are only stable for approximately 42 days at 4° C. and cannot be sterilized and thus are impractical on the front-lines or extended natural disaster scenarios (Winslow, 2003). Indeed, RBCs and pRBCs are known to decrease in effectiveness in as little as five days (Keidan et al., 2004). The ever increasingly limited availability of fresh, pathogen free, human blood products for transfusion in emergency and non-emergency situations has led to the development of hemoglobin-based oxygen carriers (HBOCs) (Winslow, 2003; Lowe, 2006a, 2006b; Stollings and Oyen, 2006; Moore et al., 2006; Alayash et al., 2007).

HBOCs have undergone several developmental generations since research first began on blood substitutes in the early 1900s (Winslow, 2003; Sellards and Minot, 1916). Toxicity effects due to hemoglobin extravasation, glomerular filtration rates, and NO redox chemistry have proven to be a major hurdle for the clinical application of HBOCs (Dunne et al., 2006; Beuhler and Alayash, 2004; D'agnillo and Alayash, 2000; Bonaventura et al., 2007; Tsai et al., 2006). Monomeric or non-crosslinked hemoglobins dissociate and lead to nephrotoxicity. Monomeric, dimeric, and small polymeric HBOCs are too small to remain in the laminar flow of small blood vessels and therefore can approach or extravasate into the vascular endothelia and react with NO resulting in vasoconstriction, and the high colloid osmotic pressure and blood viscosity from HBOCs affect blood flow and sheer stress on the vasculature (Buehler and Alayash, 2004).

In addition to the need for HBOCs in cases of blood loss, countless numbers of patients suffer from chronic wounds such as diabetic ulcers or various forms of necrotizing fasciitis that often develop from the body's inability to sufficiently oxygenate damaged or poisoned tissues (Young et al., 2006; Strauss, 2005). Chronic foot ulcers affect 4-10% of the diabetic population resulting in 50-80% of all lower extremity amputations (Lavery et al., 1996, Boulton, 1995; Reiber, 1996). These conditions are often relieved through amputation, surgical intervention, and/or hyperbaric oxygen treatment, which are invasive or not commonly available and expensive. These could be replaced with a simple, localized, topical oxygenating treatment (Young et al., 2006, Widjaja et al., 2005, Fife et al., 2007, Gill and Bell, 2004; Jallali et al., 2005).

Tissue engineering and tissue regeneration require controlled and sustained oxygenation for optimal growth and function. The lack of sufficient oxygen diffusion is one of the greatest current hurdles in tissue engineering and limits the size of tissues that can be regenerated or engineered (Harrison et al., 2007; Khademhosseini et al., 2007). Adequate, targeted, oxygen delivery to hypoxic or injured tissues via hemoglobin-based oxygen carriers (HBOCs), either in vivo or in vitro, is crucial to accelerate wound healing and tissue regrowth, delay or prevent the onset of necrosis, and decrease the mortality rate of trauma patients.

There is an additional and increasing need for HBOCs to extend the biological capabilities of emergency responders and war fighters beyond current physiological capacity under extenuating and harsh environmental circumstances that often lead to exhaustion, hypoxia, hypothermia, and death. Altitudinal $P_{O2}$ levels vary from ~160 mmHg at sea level to only ~95 mmHg at 4000 m, which is the typical altitude of the Hindu Kush mountain range passes on the border of Afghanistan and Pakistan. The brain is the organ most dependent on blood oxygen levels, and consumes ~20% of available oxygen (Erekińska and Silver, 2001). Thus, the initial effects of hypoxia and hypothermia often lead to confusion and loss of consciousness, impeding emergency rescue results and military operational success (Erekińska and Silver, 2001, Rossen et al., 1943). Emergency rescue efforts and military operations can be enhanced by the ability to undergo substantial hypoventilation/submersion, or extreme physical activity without exhaustion for extended periods of time, all aided by tissue oxygenation from intelligent HBOCs. Moreover, US military response to developing situations in demanding high-altitude arenas is hampered by the necessity to acclimate war fighters, sometimes for weeks, before deployment (Muza, 2007). The ability to rapidly increase potential oxygenation, in preparation for or in response to extensive physical activity, hypoxia, or hypothermia, is of paramount importance to emergency first responders and war fighter deployment.

The need for controlled and targeted oxygenation of tissues, either in vivo (trauma, stroke, ischemia, hypoxia, hypothermia, wound healing, fatigue) or in vitro (tissue engineering), has instigated substantial research efforts to develop blood substitutes, consisting of both volume expanders and oxygen therapeutics. Hemoglobin-based oxygen carriers (HBOCs) have great potential over other oxygen delivery methods, such as perfluorocarbons or silicone oils, to deliver oxygen because of their biocompatibility and inherent sensitivity to physiological changes in oxygen partial pressure ($P_{O2}$) necessary for $O_2/CO_2$ exchange and respiration.

Much progress has recently been made in the field of HBOCs; however, despite more than 30 years of research and several design iterations, HBOCs still suffer from stability and toxicity related issues resulting from the NO scavenging and redox associated side-reactions of an acellular heme group and over-oxygenation of normoxic tissues (Natanson et al., 2008; Winslow et al., 2003). A stable, biocompatible (non-toxic), tunable HBOC system that indefinitely sequesters the hemoglobin from the vasculature and intelligently responds to physiological cues to specifically deliver oxygen to hypoxic/ischemic tissues only where and when required is urgently required.

Current HBOC technology typically relies on (i) manipulations of human or bovine hemoglobin (e.g. stroma free, cross-linked, polymerized, and chemically modified) and (ii) encapsulation of such for delivery by a variety of methods including liposomes, silica particles, hydrogels, and polymerization. Human or bovine hemoglobin has traditionally been used in these research efforts because of its ease of access and non-immunogenicity in a human system. Many of the current encapsulation technologies result from pharmaceutical and drug delivery research, in which the formulation slowly dissolves to deliver the enclosed payload at a specified rate. When using this type of delivery platform, other hemoglobin variants, which might provide improved oxygen delivery profiles, often have not been used out of immunogenicity/toxicity concerns. Due to the toxicity of the acellular heme group, no HBOCs have heretofore been available for clinical use, beyond compassionate care, in the United States (June 2008).

Recent reviews of the current HBOC treatments under production or recently involved in clinical studies reveal a significant increase in the rate of death, myocardial infarction, hypertension, and renal toxicity (Natanson et al., 2008; Buehler and Alayash, 2004; D'agnillo and Alayash, 2000; Bonaventura et al., 2007). It is gravely apparent that given the dire need for life-saving blood substitutes and the toxicity of the current methodologies, a new pathway toward effective HBOCs must be pursued.

The present invention is directed to overcoming or at least reducing the effects of one or more of the problems set forth above.

SUMMARY OF THE INVENTION

The present invention provides a delivery system for hemoglobin in which the hemoglobin is isolated from the vasculature in its functional form. This prevents toxicity of the heme in medical uses. Because the hemoglobin is isolated from the vasculature, the delivery system allows the use of a variety of hemoglobins which differ in their oxygen dissociation profiles, including mutant hemoglobins from other species.

The invention provides an alternative to prior encapsulation methods, and is biocompatible, stable (i.e., it does not dissolve away and thereby expose the heme), and able to irreversibly bind and hold large amounts of functional hemoglobin variants.

The invention provides a carbide-derived-carbon hemoglobin-based oxygen carrier (CDC HBOC). The CDC HBOC utilizes novel materials, methods, and designs to enhance war fighter performance in high-altitude, adverse conditions, or submersion, and provides a safe and effective blood substitute for combat casualty care. In an alternative embodiment, the invention provides CDC for oxygen delivery in the absence of attached hemoglobin (CDC OC).

The invention provides an oxygen delivery system, comprising either carbon-derived carbide to which hemoglobin is irreversibly adsorbed, or carbon-derived carbide in which pore size is tuned to reversibly adsorb $O_2$. The oxygen delivery system additionally may comprise a hydrogel coating. The hydrogel coating comprises an interpenetrating network which swells and increases pore size in response to decreasing temperature and/or decreasing pH. The hemoglobin is a variant or mutant having an oxygen dissociation profile which differs from that of human hemoglobin, and preferably is a variant or mutant which has a higher affinity for oxygen than human hemoglobin.

The oxygen delivery system additionally may comprise an enteric coated shell which dissolves at the pH of the small intestine. This formulation can be administered orally. Alternatively, the oxygen delivery system can be produced in the form of a powder, which is especially suitable for topical administration. In another embodiment, the oxygen delivery system additionally comprises a physiologically suitable carrier for parenteral administration. This formulation can be administered either intravenously or subcutaneously. In a further embodiment, the oxygen delivery system is formulated as a nebulized inhalant.

Additional delivery designs include a smaller CDC particle, 50-70 nm in diameter, surrounded with an intelligent hydrogel coating for a total diameter of 150-200 nm. This approach will still allow CDC HBOC passage through the alveoli into the blood stream. Slow decomposition of the outer hydrogel coating will provide for eventual clearance of the CDC HBOC from the blood through the glomerulous, thus circumventing any toxicity related to non-biodegradation.

BRIEF DESCRIPTION OF THE DRAWING

The foregoing advantages and features of the invention will become apparent upon reference to the following detailed description and the accompanying drawing which is a schematic of the CDC HBOC according to the invention, which shows carbide-derived carbon (CDC) adsorbent substrate 1, adsorbed variant or mutant hemoglobins 2, and optional associated heme maintenance proteins such as super oxide dismutase (SOD) 3 and catalase (CAT) 4, optional pH and temperature responsive intelligent hydrogel coating 5, and final formulation as powder 6, nebulized mist 7, or capsule 8.

DETAILED DESCRIPTION OF SPECIFIC EMBODIMENTS

A novel carbide-derived-carbon hemoglobin-based oxygen carrier (CDC HBOC) according to the invention irreversibly sequesters hemoglobin and is tunable on multiple levels for adaptability and broad spectrum use. In an alternative embodiment, pore size is tuned to tailor the CDC for $O_2$ adsorption directly, thereby providing a non-hemoglobin-based oxygen carrier (CDC OC) which reversibly sequesters $O_2$ without the requirement for adsorbed hemoglobin. The resulting carriers can be used to deliver oxygen to a patient in need, to tissues in culture, and in non-medical applications.

Figure 1:
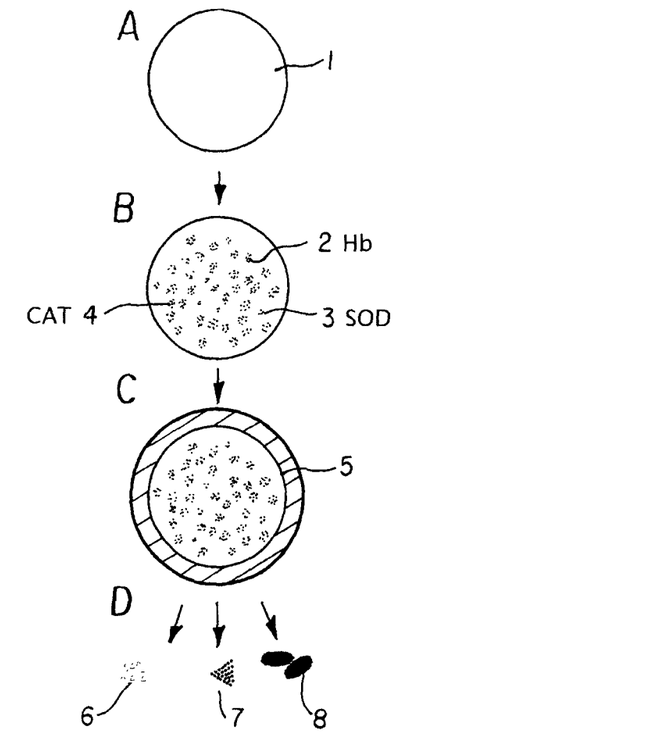

The drawing shows the three primary components of CDC HBOC:

(i) a micron scale (~0.2 μm) carbide-derived carbon (CDC) adsorbent substrate 1 with 5-6 nm pores, (ii) adsorbed variant or mutant hemoglobins 2 with unique and appropriate oxygen dissociation profiles and Hill coefficients and optional associated heme maintenance proteins such as super oxide dismutase (SOD) 3 and catalase (CAT) 4, and (iii) an optional pH and temperature responsive intelligent hydrogel coating 5 to control the release of oxygen to target only hypoxic or hypothermic tissues.

The drawing shows final formulation as powder 6, nebulized mist 7, or capsule 8, although other formulations are possible, as described herein.

The hemoglobin-based oxygen carrier according to the invention provides functional hemoglobin (mutant or wild type) which is greater than or equal to that of packed red blood cells (pRBCs). The functional hemoglobin is stably and irreversibly adsorbed onto a nanoporous carbide-derived carbon (CDC) platform for prolonged and controllable oxygen delivery. The HBOC platform is tunable, polymorphic, polyfunctional, and fully biocompatible, and is usable in broad applications, such as a topical treatment for acute and chronic wound healing, as an ingestive for increased respiratory capacity and tissue oxygenation, as a suspension for intravenous transfusion, and as an oxygenation supplement in tissue engineering matrices to enhance tissue production variety, growth rate, and size. An additional, although non-medical, application of the technology is as an oxygen source for underwater fuel cells (Davies and Moore, 2007).

The CDC HBOC according to the invention preferably is a CDC HBOC which is surrounded by an optional semi-permeable hydrogel shell, thus providing three-fold tunability. That is, each of the CDC, hemoglobin variant or mutant, and hydrogel shell can be altered and optimized to meet the specific needs of a given scenario for in vitro and in vivo applications, thereby providing a single platform for broad spectrum use. The three components are discussed in more detail below.

Tunable CDC

The first component of the CDC HBOC, which provides the platform for hemoglobin delivery, is carbide-derived carbon (CDC). CDC is produced by the extraction of metals from the carbon lattice in ceramic metal carbides, such as $Ti_2AlC$ and SiC. A metal carbide can be milled on the micrometer scale and CDC is typically produced by etching out the metal with chlorine gas at temperatures ranging from 300-1200° C. at variable flow rates and volumes (Nikitin and Gogotsi, 2004). This inexpensive process leaves a lattice composed solely of carbon with a very large surface area, from 1000 to 2300 $m^2/g$ and 50-80% porosity. Even unoptimized CDC with a surface area of ~2300 $m^2/g$ is capable of adsorbing functional hemoglobin at several times its own mass.

By altering the choice of the initial metal carbide composition and structure, and the temperature, type, and flow of the etching gas, the CDC pore size and shape, as well as the percent porosity, can be controlled. Pore size can be controlled with ~1-5 Å precision at a pore range of 0.6-10 nm. Pore sizes up to 500 nm can be created using porous carbide ceramics as precursors, albeit with reduced precision (Yushin et al., 2005). Hundreds if not thousands of different CDC samples of varying initial composition, pore size, porosity, macrostructure (powders, films, monoliths), and treatments have been fabricated and tested.

CDC is unique in that it is a nanoporous material in which pore size is not coupled to particle size. Therefore, it is unlike carbon nanotubes or nanohorns. CDC displays high surface area and high adsorptivity, without necessarily being nanoparticulate (<100 nm diameter). In order to prevent extravasation, glomerular filtration, and to maintain laminar vascular flow, the CDC HBOC is designed to be larger than particles known to cause toxicity due to their nanoparticulate size, yet still small enough to allow fluid passage through the capillaries. CDC used as the platform for HBOC according to the invention preferably has 100-200 nm diameter, which is somewhat larger than what is considered truly nanoparticulate, thereby avoiding the deleterious side effects that are sometimes observed with nano-sized materials. With its surface area up to 2300 $m^2/g$ and high adsorbate avidity, CDC is capable of outperforming all current HBOCs under development in oxygen delivery per weight of HBOC.

Carbon is biologically compatible and has been shown to not illicit an immune response (Brooks et al., 2004), and carbide-derived carbons are very similar to activated charcoal in their structure and surface chemistry. The biological compatibility provided by the carbon addresses a key requirement for a HBOC.

By varying starting material composition and structure, demetallization gas temperature and flow rate, and surface treatment during preparation of the CDC substrate, it is possible to produce substrates which vary in particle size, pore size, and porosity. This enables the substrate to be optimized to have the most advantageous characteristics for adsorption of functional hemoglobin and tissue oxygenation, so that it irreversibly adsorbs functional hemoglobin.

Due to the large surface area and tunable pore size, CDCs have been shown to specifically target and adsorb extremely large quantities of small molecules such as $H_2$ and methane (Yushin et al., 2006b), as well as large biomolecules such as interleukins (Yushin et al., 2006a), from either a gas or liquid phase. Tuning of the pores selectively targets molecules of similar size for adsorption to the carbon lattice.

CDC pore size can be optimized for hemoglobin (either $\alpha_2\beta_2$ tetramers or disulfide-linked $\alpha_4\beta_4$ octamers). Data show that pore sizes can be tailored to specifically adsorb hemoglobin with a tetrameric diameter of 5.5 nm and a cross-linked octameric ellipsoid major axis of ~11 nm. Tuning of pore size increases both the amount of hemoglobin adsorbed and the heme stability because the protein penetrates the pores and is protected from external reactants as well as tetramer dissociation. Toxicity also is reduced by the ability to control pore size so that most of the hemoglobin is sequestered inside the CDC, away from direct contact with the tissue vasculature.

Alterations in the CDC fabrication process can change the particle size and hydrophobicity, the pore size and shape, as well as the percent porosity. The pore size can be controlled with Angström-level precision and can be made to facilitate the additional adsorption of ancillary proteins such as superoxide dismutase (SOD), catalase (CAT), methemoglobin reductase (MHbR), and oxidative stabilization with organic molecules such as ascorbic acid and NADH help to stabilize maximize the lifetime of the heme group and serve to mitigate the oxidation of the heme iron and the formation of inactive methemoglobin (MHb). They also minimize possible redox side-reactions.

Functionalization of the carbon lattice can be used to further increase the specificity and selectivity for adsorbate molecules of similar size. For example, the substrate can be made to be more hydrophobic or hydrophilic dependent upon the class and size of ligand that is used for functionalization. Functionalization thus can be used to enhance the solubility.

Another benefit of functionalization is that it can facilitate the additional co-adsorption of the ancillary proteins such as superoxide dismutase (SOD), catalase (CAT), methemoglobin reductase (MHbR), and oxidative stabilization with organic molecules such as ascorbic acid and NADH to maximize the lifetime of the heme group and minimize possible redox side-reactions. This increases the stability, prolongs oxygen delivery capability, and reduces toxicity of the CDC HBOC.

Since the CDC carbon lattice is composed mostly of $sp^2$ hybridized carbons, several techniques are available for direct coupling of molecules that will lend differential properties to the surface of the carbon. Aryl diazonium coupling yields the most stable linkage (carbon-carbon bond) (Bahr and Tour, 2001; Pagona et al., 2008), but other techniques such as carboxylate-amidation or silanization can also be used (Li et al., 2005).

Optimization of the CDC fabrication process maximizes hemoglobin adsorption and $O_2$ delivery potential, and provides the first level of tenability according to the present invention.

Tunable Hemoglobin

The second major component of the CDC HBOC is hemoglobin. Hemoglobin is a globular 65 kDa tetrameric protein ($\alpha2\beta2$), which is roughly 5.5 nm in diameter. It is found in mM concentrations within erythrocytes. Each monomer includes an iron bound porphyrin ring or heme prosthetic group that reversibly binds oxygen containing molecules such as $O_2$, CO, and NO. A great deal is known about the structure and function of hemoglobin and the mechanism of ligand association to the heme.

In humans, the hemoglobin concentration in the blood is approximately 12-1.6 g/dL and delivers oxygen obtained from the alveolar capillaries, where the heme group exchanges $CO_2$ for $O_2$, to the vasculature of oxygen starved tissues, where it releases the $O_2$ to be replaced by $CO_2$, returning to the alveoli in a cyclical process. The pH dependence of hemoglobin affinity for oxygen (Bohr Effect) enhances this exchange as the pH of hypoxic tissues is reduced (Giradina et al., 2004). The cooperative delivery of oxygen by the four hemoglobin subunits ($\alpha 2\beta 2$) is dictated by the oxygen dissociation curve in response to changes in $O_2$ partial pressure ($PO_2$) and is characterized by the $P_{50}$ (partial pressure of oxygen at 50% hemoglobin saturation) and $n_{50}$ (Hill coefficient at 50% hemoglobin saturation) values. Mutations in the hemoglobin primary structure, especially surrounding the heme pocket and subunit interface, affect the $P_{50}$ and $n_{50}$. In many circumstances, organisms have taken advantage of such mutations in order to flourish under conditions of low $P_{O2}$ (Giradina et al., 2004; Windslow, 2007; Weber, 2007; Storz, 2007).

The physiologic response to hypoxia involves redox-sensitive signaling pathways linking extracellular stimuli to gene regulation through the hypoxia-inducible factor (HIF-1$\alpha$) (Zhu and Bunn, 1999, 2001). Therefore, upregulation of the HIF-1$\alpha$ gene can be an effective in vivo and in situ reporter of cellular responses to environmental hypoxic conditions.

Since atmospheric $P_{O2}$ decreases with altitude—at 4000 m the alveolar $P_{O2}$ approximates capillary $P_{O2}$ at sea level (20-30 mmHg)—doping the blood with HBOCs based on current wild-type human or bovine hemoglobin does not provide a significant increase in tissue oxygenation. Additionally, allosteric effectors on hemoglobin oxygenation such as blood pH and $Cl^-$, 2,3-DPG, and ATP concentrations cannot vary substantially without deleterious side-effects. Furthermore, treatment of hemorrhagic shock with current HBOCs has been shown to increase the rate of myocardial infarction and renal failure due putatively to extravasation and hemoglobin tetramer dissociation. Therefore, the most effective way to increase tissue oxygenation and save lives in response to either trauma or hypoxic conditions with a HBOC is to increase/restore the amount of hemoglobin present in the blood or at the site of a wound with high concentrations of hemoglobin variants that possess desirable oxygen dissociation profiles without exposing the vasculature to the toxic heme group while maintaining physiological osmotic pressure. Thus, in a preferred embodiment, the CDC HBOC platform incorporates a hemoglobin variant or mutant selected to have a particular oxygen dissociation profile, particularly by using a variant of mutant with an affinity for oxygen that is higher than that of human hemoglobin.

High-altitude species have evolved a number of mechanisms to adapt to life in low oxygen environments. Several of these mechanisms are physiological and include increased ventilation rate and increased hematocrit or 2,3-DPG concentrations. However, other adaptations are biomolecular and are based in the structure of the hemoglobin molecule itself. Recombinant hemoglobin molecules comprising both naturally-occurring and laboratory-generated mutants have been developed in an effort to understand and exploit the varying oxygen binding properties of hemoglobin. These include naturally-occurring variants found in high-altitude and other species (Winslow, 2007; Jessen et al., 1991; Weber, 2007), as well as site-directed mutagenesis derived recombinant mutants based on structural studies specifically designed to alter the $P_{50}$ or $n_{50}$ (Jeong et al., 1999; Tsai and Ho, 2002;

Fang et al., 1999; Tsai et al., 2000; Wiltrout et al., 2005). Hundreds of these recombinant hemoglobin variants are maintained by Dr. Chien Ho of Carnegie Mellon University.

In addition, hemoglobin mutants have been designed previously with the intention of using them as blood substitutes, but their small size makes them unsuitable for use alone, and they must be incorporated into a suitable platform for delivery. The combination of specific hemoglobin mutants with the CDC platform in the present invention provides for excellent delivery of oxygen, while mitigating toxicity. Suitable oxygen dissociation profiles for specific HBOC applications are achieved by CDC adsorption of appropriate recombinant novel hemoglobin variants and mutants exhibiting altered $P_{50}$ and $n_{50}$ parameters. Table 1 shows $P_{50}$ and $n_{50}$ of some of the currently available prokaryotically expressed wild type and recombinant mutant hemoglobins.

TABLE 1

| Hemoglobin | $P_{50}$ (mm Hg) | $n_{50}$ |
|---|---|---|
| Hb A | 8.0 | 3.1 |
| rHB ($\alpha$V96W) | 12.8 | 2.8 |
| rHB ($\beta$L105W) | 28.2 | 2.6 |
| $rHB_{Presbyterian}$ ($\beta$N108K) | 24.5 | 2.9 |
| $rHB_{Yoshizuka}$ ($\beta$N108D) | 15.5 | 2.9 |
| rHB ($\beta$N108Q) | 17.4 | 3.1 |
| rHB ($\beta$N108R) | 28.9 | 3.1 |
| rHB ($\beta$N108E) | 24.1 | 2.9 |
| rHB ($\beta$N108A) | 23.1 | 3.1 |
| rHB ($\alpha$V96W, $\beta$N108K) | 48.8 | 2.3 |
| rHB ($\alpha$V96W, $\beta$N108D) | 18.6 | 2.6 |
| rHB ($\alpha$L29F, $\beta$N108Q) | 12.1 | 2.8 |

Table 1 shows that known recombinantly designed hemoglobin mutants include mutants that have $P_{50}$ values similar to wild-type, as well as mutants that have either higher or lower $O_2$ affinity. Thus, a hemoglobin mutant with a desired $P_{50}$ can easily be incorporated into the CDC HBOC according to the invention.

Recently, hemoglobin expression in heterologous eukaryotic and prokaryotic systems has been achieved (Weickert et al., 1999; Shen et al., 1997), and techniques to increase the quantity and rate of production of functional hemoglobin have been undertaken (Shen et al., 1997).

Hemoglobin sequence alignments, consisting of high- and low-altitude, and mammalian and non-mammalian homologues, as well as detailed structural and mechanistic analysis, followed by relevant site-directed mutagenesis of human hemoglobin can produce hundreds of variants with different $O_2$ dissociation profiles resulting from diverse $P_{50}$ levels and Hill coefficients ($n_{50}$). One or multiple types of hemoglobin can be adsorbed to the CDC substrate dependent upon the prescribed HBOC application for targeted oxygen delivery. Table 2 shows how variants and mutants can be selected and/or combined to provide desired oxygen delivery.

TABLE 2

| Hemoglobin | Conformation | ~$P_{50}$ (mmHg) |
|---|---|---|
| HbA | Tetramer | 8 |
| $\alpha\alpha$Hb | Tetramer (cross-linked) | 30 |
| rHb($\alpha$L29W) | Tetramer | 32 |
| rHb($\alpha$N78C) | Octamer | 10 |
| rHB($\alpha$L29F, N78C) | Octamer | 6 |

Oxygenation of only those tissues that are hypoxic is achieved by selecting wild-type or recombinant mutants with appropriate oxygen dissociation profiles for the specific task (trauma, high-altitude, tissue engineering) and by providing superior hemoglobin density per unit HBOC. Increased hemoglobin density per unit HBOC also resolves concerns over increases in osmotic pressure upon HBOC treatment, as fewer particles are required to achieve the same level of oxygenation.

Selection of suitable hemoglobin variants and mutants for the CDC HBOC provides a second layer of tunability, as incorporation of the appropriate mutant tailors the HBOC to a specific desired application.

Tunable Hydrogel Shell

In addition to the CDC and adsorbed hemoglobin, the CDC HBOC according to the invention additionally may comprise an optional hydrogel shell. The hydrogel shell is an interpenetrating network (IPN) hydrogel, such as poly(N-isopropylacrylamide) (pNIPA) or carrageenan alginate (CarAlgi), which are designed to swell and increase their pore size in response to decreasing temperature (hypothermia) and pH (hypoxia) in the physiologically relevant range for humans. Under such conditions, the increase in pore size and a concomitant decrease in $O_2$ dissolution pathway tortuosity leads to an increase in oxygen diffusion from the hemoglobin adsorbed CDC. Variations in hydrogel composition, concentration, and extent of cross-linking allow fine tuning of oxygen delivery dependent upon the required application. The hydrogel coating also increases the biocompatibility of the CDC HBOC. The hydrogel coating is optional, but can be used to mitigate CDC toxicity as needed, depending on the other components selected.

The incorporation of a hydrogel coating lends an additional degree of tunability for increased environmentally sensitive oxygen delivery and also aids in reducing possible toxicity of the carbon particles by surrounding them with a temperature and pH responsive biocompatible layer.

Tuning and Evaluation of CDC HBOC

Biocompatibility of CDC and CDC adsorbed hemoglobins can be determined by using cellular assays and genomic marker arrays to evaluate biomarkers of inflammation/injury (IL-6 and LDH release), cell morphology, and toxicogenomic analysis of HEK-293 cells following exposures to CDC and CDC adsorbed hemoglobins.

Inflammatory response of HEK-293 cells upon addition of hemoglobin solutions or CDC HBOC is evaluated by analysis of cell released cytokines (IL-6) into the culture media following standard protocols. Oxidative stress is evaluated by the release of LDH into the media and staining cells for oxidative markers of DNA damage (8-hydroxy-2' deoxyguanosine (8OHdG)). Gene arrays are used to evaluate the potential up and/or down regulation of genes indicative of toxicological potential. Morphologic and biochemical changes related to apoptosis or necrosis also are evaluated.

All of these analyses are performed at the termination of each 2 or 4 hour hypoxic cell study. LDH and IL-6 are evaluated in culture media at the termination of each hypoxic study by ELISA-based assays (QuantiChrom™ and eBioscience™). Cells are stained for 8-OHdG using an antibody-based staining system (Genox corp.). Additionally, cells are processed to ultimately obtain cDNA which is evaluated using microarray platforms (Axon Instruments, Inc.).

The stability and longevity of the heme group of CDC adsorbed hemoglobin is assessed using FT-IR experimentation using a Nicolet 6700 FT-IR spectrophotometer equipped with an Attenuated Total Reflectance prism and gas purge lines connected to 1% and 21% $O_2$ gas mixtures. Analysis of the region from ~450-700 nm, and additionally the spectral region at ~950 nm, allows for the differentiation among the Hb, $HbO_2$, HbCO, and MHb heme species (Zijlstra et al., 1991). These experiments, repeated over hours or days of exposure, can then be used to determine the length of stability and rate of interconversion of the heme group in CDC adsorbed hemoglobin as compared to hemoglobin in solution.

The optimal oxygen carrying capacity of hemoglobins when adsorbed to CDC can be evaluated in several ways. First, an in situ system employing human embryonic kidney cells (HEK-293) can be used. This in situ system is routinely employed in conjunction with in vivo studies of modified hemoglobin solutions, and is used to evaluate the activation/suppression of HIF-1α upon exposure to selected CDC HBOCs. HIF-1α is a reliable biomarker of cellular oxygen deliver (Manalo et al., in press), being suppressed at optimal oxygen concentrations. The dose dependent suppression of HIF-1, its target genes and gene regulated proteins by CDC-adsorbed hemoglobins is evaluated using a combination of gene arrays and protein analysis in treated cells. The ability of CDC-adsorbed hemoglobins to off load oxygen in situ is evaluated in HEK-293 cells subjected to normoxia (21% $O_2$) and severe hypoxia (1% $O_2$).

Gene arrays and protein analysis of downstream hypoxia sensitive elements induced by HIF-1α serve as markers of optimal oxygen delivery. CDC-adsorbed hemoglobin as well as equal amounts of soluble hemoglobin are added separately to individual plates containing cultured HEK-293 cells. Plates containing cells plus oxygen carriers at differing concentrations are added to a hypoxic chamber maintained at 1% $O_2$ for either 2 or 4 hours. At the end of 2 or 4 hours, cells are processed to evaluate HIF-1α protein expression by Western blotting, and downstream gene expression (erythropoietin (EPO), heme oxygenase (HO-1), nitric oxide synthase (iNOS/eNOS, cytochrome oxidase (COX4-2) using Real time PCR Applied Biosystems (ABI) TaqMan® Gene Expression Assays system. Additionally, protein expression resulting from HIF-1α induced gene activation is measured either in the culture media (EPO release) or in cells (iNOS/eNOS, HO-1 and Cox4-2) using ELISA or Western blot analysis, respectively.

At baseline, 0.5, 1, 2, 3 and 4 hours, media are sampled (50 µL) from each dish without breaching the chamber to analyze the hemoglobin iron oxidative state via diode array spectrophotometry and 10 µL is frozen for later analysis by mass spectrometry to identify potential oxidative modifications and changes within the hemoglobin protein. This evaluation is critical to assessing the percentage of the $O_2$ carrying ferrous form of hemoglobin in culture media and the stability of the heme/protein over the duration of the experiment.

Alternatively, oxygen delivery can be tested by oxygen electrode. After washing with 1×PBS, the hemoglobin-adsorbed CDC sample is resuspended in 5 ml of 1×PBS pH7.4 and placed in a dissolved oxygen electrode chamber. Following calibration and oxygenation with a 95% $O_2$ gas mixture, 1% $O_2$ is allowed to flow through the chamber at approximately 5 psi (gauge) for three minutes, after which the chamber is sealed under positive pressure. The drop in $O_2$ concentration in the buffer is monitored by the oxygen electrode over the period of minutes to hours and recorded. The rate of decay of oxygen in the buffer is compared for CDC alone and CDCs with adsorbed wild-type and recombinant mutant hemoglobins. Oxygen delivery capability for $O_2$ adsorbed directly to CDC is performed in a similar manner.

Formulation and Administration

The CDC HBOC and CDC OC both can be packaged into enteric coated shells for delivery into blood stream via absorption through the small intestine. Alternatively, they can be formulated as a powder for topical administration, with a physiologically suitable carrier for parenteral use (including both intravenous and subcutaneous administration), or as a nebulized inhalant for direct delivery into the circulatory system through the alveoli, to provide increased respiratory capacity and tissue oxygenation. The CDC HBOC and CDC OC also can be formulated as an oxygenation supplement in tissue engineering matrices to enhance tissue production variety, growth rate, and size. A further, although non-medical, application of the technology to be developed is as an oxygen source for underwater fuel cells.

Advantages of CDC HBOC

CDC HBOC according to the invention is superior to current HBOCs for the following reasons:

(1) Less expensive large-scale production due to continuing improvements in yield and the pathogen (HIV, HAV, BSE) free nature of prokaryotic expression systems and the inexpensive nature of the CDC substrate (less than 10 cents/gram), (2) Reduced toxicity due to the relatively large CDC particle size and irreversible hemoglobin adsorption, and (3) Efficient targeted oxygenation due to the high surface area and absorptivity of the CDC material as well as choice of hemoglobin adsorbed.

Example 1

Pre-milled starting metal carbides of $Ti_2AlC$ powder (100-200 nm) were loaded into the hot zone of an Ar purged horizontal quartz tube furnace. After the required temperature was achieved (200-1200° C.), the Ar gas was replaced by 99.5% $Cl_2$ gas at 1000° C. for 3 hours flowing at a rate of 10 sccm. The samples were then cooled under flow of Ar to remove residual metal chlorides with a post treatment of 5% $H_2$ gas at 600° C. for 2 hours, or a similar treatment with $NH_3$ gas. The final CDC product was then sealed under vacuum until further use.

Following synthesis and treatment, CDC porosity was determined by sorption in nitrogen at 77K and carbon dioxide at 273K and the specific surface area was calculated from the Brunauer-Emmett-Teller (BET) method. The pore size distribution was determined using Non Local Density Functional Theory (NLDFT). Pore size was 4-6 nm. Additional characterization was performed by SEM, TEM, and SAXS.

Example 2

Hemoglobin adsorption was achieved by adding 1-10 mg of the CDC of Example 1 to 1 ml of 50 mg/ml αα cross-linked hemoglobin (ααHb) solution in 1×PBS at pH 7.4 at 4° C. for 1 hour. Adsorption was conducted in 1.5 ml microcentrifuge tubes at 4° C. and pH 7.4. Following adsorption, the CDC is washed three times for 10 minutes each with 1×PBS pH 7.4 at 4° C. and monitored as above for hemoglobin desorption. Adsorption of hemoglobin to the CDC was quantified by optically monitoring the time-dependant decrease in absorbance of the hemoglobin solution by UV/Vis spectrophotometry according to the Winterbourne equation (Winterbourne, 1990). There was no observed increase in adsorbed hemoglobin after approximately one hour. Under conditions of high ααHb concentration and low CDC concentration, adsorption of ααHB at several times the weight of the CDC substrate was detected. Furthermore, it was observed that the ααHb did not desorb significantly even after 16 hours at physiological temperature.

An average unit of pRBCs typically contains ~63 g of hemoglobin in ~450 ml. The results here show that delivery of equivalent amounts of hemoglobin with the same oxygenation capacity with non-optimized CDC HBOC can require as little as 3 ml of 10 mg/ml CDC HBOC. Compared with 1 unit (250 ml) of 10% diaspirin-crosslinked hemoglobin (DCLHb) that contains 25 g hemoglobin (Schubert, 2003), CDC HBOC has the potential to deliver a much larger amount of hemoglobin per unit HBOC.

Testing of the $O_2$ delivery capacity of ααHb adsorbed CDC showed gradual oxygenation over time until $P_{O2}$ levels were re-established. Four ml of 1×PBS buffer pH 7.4 containing varying amounts of CDC was placed in an enclosed sampling chamber at room temperature with 1% oxygen gas mixture flowing through the chamber for three minutes and then sealed under positive pressure. The chamber was constructed of a polaragraphic Clark-type oxygen electrode inserted into the hypoxic chamber through a hole that was later sealed with silicone sealant. The oxygen electrode was situated such that the probe tip was fully immersed in the CDC HBOC containing buffer to be evaluated. The diffused oxygen content of the buffer was measured over time by the oxygen electrode. Non-oxygenated CDC in the absence of adsorbed hemoglobin did not provide oxygenation, while the other samples with adsorbed hemoglobin showed a concentration dependent oxygen delivery profile. Even after one week, hemoglobin adsorbed CDC was still able to oxygenate the buffer to a certain extent.

Thus, a CDC HBOC has been described according to the present invention. Many modifications and variations may be made to the techniques and structures described and illustrated herein without departing from the spirit and scope of the invention. Accordingly, it should be understood that the products and methods described herein are illustrative only and are not limiting upon the scope of the invention.

The contents of all documents mentioned herein are incorporated by reference in their entirety.

LITERATURE CITED

Alayash, A. I., D'Agnillo, F., Buehler, P. W. (2007) First generation blood substitutes: what have we learned? Biochemical and physiological perspectives *Expert Opin. Biol. Th.* 7, 665-675.

Bahr, J. L., Tour, J. M. (2001) Highly functionalized carbon nanotubes using in situ generated diazonium compounds *Chem. Mater.* 13, 3823-3824.

Bellamy R F. (1984) The causes of death in conventional land warfare: implications for combat casualty care research *Mil. Med.* 149:55-62

Bonaventura C., Henkens, R., Alayash, A. I., Crumbliss, A. L. (2007) Allosteric effects on oxidative and nitrosative reactions of cell-free hemoglobins *IUBMB Life* 59, 498-505

Bonnie. R. J., Fulco, C. E., Liverman, C. T., eds. Reducing the burden of Injury: advancing prevention and treatment. In: Committee on Injury Prevention and Control: magnitude and costs. National Academy Press: Washington; 1999:41-59.

Boulton A. J. M. The pathway to ulceration: aetiopathogenesis, In: Boulton A. H. M., Connor H., Cavanagh P. R., editors. The foot in diabetes ($2^{nd}$ edn). Chichester: John Wiley and Sons, (1995): 37-48

Brayner, R. (2008) The toxicological impact of nanoparticles, *Nanotoday* 9, 48-55.

Brooks, R. A., Jones, E., Storer, A., Rushton, N. (2004) Biological evaluation of carbon-fibre-reinforced polybutyleneterephthalate (CFRPBT) employed in a novel acetabular cup, *Biomaterials* 25, 3429-3438.

Buehler, P. W., Alayash, A. I. (2004) Toxicities of hemoglobin solutions: in search of in-vitro and in-vivo model systems *Transfusion* 44, 1516.

Buehler, P. W., D'Agnillo, F., Hoffman, V., Alayash, A. I. (2007) Effects of endogenous ascorbate on oxidation, oxygenation, and toxicokinetics of cell-free modified hemoglobin after exchange transfusion in rat and guinea pig *J. Pharmacol. Exp. Ther.* 323, 49

Burton R. A., Tsurupa G., Medved L., Tjandra N. (2006) Identification of an ordered compact structure in the recombinant bovine fibrinogen αC domain fragment by NMR. *Biochemistry-US* 45, 2257-2266.

Burton, R. A., Tsurupa, G., Hantgan, R. R., Tjandra, N., Medved, L. (2007) NMR solution structure, stability, and interaction of the recombinant bovine fibrinogen alpha C-domain fragment *Biochemistry-US* 46, 8550-8560

Champion H. R., Bellamy, R. F., Roberts, C. P., Leppaniemi, A. (2003) A profile of combat injury. *J. Trauma* 54(suppl), S13-S19.

Charlton, D. C., Peterson, M. G. E, Spiller, K., Lowman, A., Torzilli, P. A., Maher, S. A. (2008) Semi-degradable scaffold for articular cartilage replacement *Tissue Eng* A 14, 207-213.

Ciaccio, C., Coletta, A., De Saneti, G., Marini S, Coletta M. (2008) Cooperativity and allostery in haemoglobin function *IUBMB Life* 60, 112-123.

D'agnillo, F., Chang, T. M. S. (1998) Polyhemoglobin-superoxide dismutase-catalase as a blood substitute with antioxidant properties Nat. Biotech. 16, 667-671

D'agnillo, F., Alayash, A. I. (2000) Site-specific modifications and toxicity of blood substitutes The case of diaspirin cross-linked hemoglobin. *Adv. Drug Deliver. Rev.* 40, 199-212.

Davies, K. L., Moore, R. M. (2007) *IEEE J. Oceanic Eng.* 32, 365-372.

Dunne, J., Caron, A., Menu P., Alayash, A. I., Buehler, P. W., Wilson, M. T., Silaghi-Dumitrescu, R., Faiver, B., Cooper, C. E. (2006) Ascorbate removes key precursors to oxidative damage by cell-free haemoglobin in vitro and in vivo. *Biochem. J.* 399, 513-524.

Erekińska M., Silver I. A., (2001) Tissue oxygen tension and brain sensitivity to hypoxia. *Resp. Physiol.* 128, 263-276.

Fang, T. Y., Zou, M., Simplaceuanu, V., Ho. N. T., Ho, C. (1999) Assessment of roles of surface histidyl residues in the molecular basis of the Bohr effect and of beta143 histidine in the binding of 2,3-bisphosphoglycerate in human normal adult hemoglobin *Biochemistry* 38, 13423-13432.

Fife, C. E., Buyukcakir, C., Otto, G., Sheffield, P., Love, T., Warriner, R. (2007) Factors influencing the outcome of lower-extremity diabetic ulcers treated with hyperbaric oxygen therapy. *Wound Repair Regen.* 15, 322-331.

Giardina, B., Mosca, D., De Rosa, M. G. (2004) The bohr effect of haemoglobin in vertebrates: an example of molecular adaptation to different physiological requirements *Acta Physiol. Scand.* 182, 229-244.

Gill, A. L., Bell, C. N. A. (2004) Hyperbaric oxygen: Its uses, mechanisms and outcomes. *QJM-Int. J. Med.* 97, 385-395.

Godbillon, C., Sahu, S. C., Domingues, E., Fablet, C., Giovanelli, J. L., Tam, T. C., Ho, N. T., Ho, C., Marden M. C. (2006) Recombinant hemoglobin bG83C-F41Y an octameric protein. *FEBS J.* 273, 230-241.

Gogotsi Y, Nikitin, A., Ye, H. H. Zhou, W., Fischer, J. E., Bo, Y., Foley, H. C., Barsoum, M. W. (2003) Nanoporous carbide-derived carbon with tunable pore size *Nat. Mater.* 2, 591-594.

Harrsion B. S., Eberli, D., Lee, S. J., Atala, A., Yoo J. J. (2007) Oxygen producing biomaterials for tissue regeneration. *Biomaterials* 28, 4628-4634

Holcomb, J. B. (2004) Methods for improved hemorrhage control *Crit. Care* 8: S57-S60

Hoyt D. B., Bulger E. M., Knudson M. M. (1994) Death in the operating room: an analysis of a multi-center experience. *J. Trauma* 37:426-432.

Jallali, N., Withey, S., Butler, P. E. (2005) Hyperbaric oxygen as an adjuvant therapy in the management of necrotizing fasciitis *Am. J. Surg.* 189, 462-466.

Jeong, S. T., Ho, N. T., Hendrich, M. P., Ho, C. (1999) Recombinant hemoglobin exhibits low oxygen affinity and high cooperativity combined with resistance to autoxidation. *Biochemistry-US* 38, 13433-13442.

Jessen, T. H., Weber, R. E., Fermi, G., Tame, J., Braunitzer, G. (1991) Adaptation of bird hemoglobins to high altitudes: Demonstration of molecular mechanism by protein engineering *P. Natl. Acad. Sci. USA* 88, 6519-6522.

Keidan, I., Amir, G., Mandel, M., Mishali, D. (2004) The metabolic effects of fresh versus old stored blood in the priming of cardiopulmonary bypass solution for pediatric patients. *J. Thorac. Cardiov. Sur.* 127, 949-952.

Khademhosseini A., Langer, R., Borenstein, J., Vacanti, J. P. (2006) Microscale technologies for tissue engineering and biology. *P Natl Acad Sci USA* 103, 2480-2487.

Lavery L. A., Ashry, H. R., vanHoutum, W., Pugh, J. A., Harkless, L. B., Basu, S. (1996) Variation in the incidence and proportion of diabetes-related amputations in minorities. *Diabetes Care* 19, 48-52

Li, J., Vergne, M. J., Mowles, E. D., Zhong, W. H., Hercules, D. M., Lukehart, C. M. (2005) Surface functionalization and characterization of graphitic carbon nanofibers (GC-NFs) *Carbon* 43, 2883-2893.

Lowe, K. C. (2006a) Blood substitutes: from chemistry to clinic *J. Mater. Chem.* 16, 4189-2196.

Lowe, K. C. (2006b) Genomics and blood substitutes for $21^{st}$ century Europe *Artif cell. blood sub.* 34, 589-599.

Lukin J. A., Ho, C. (2004) The structure-function relationship of hemoglobin in solution at atomic resolution *Chem. Rev.* 104, 1219-1230.

Manalo, D. J., Buehler, P. W., Baek, J. H., Butt, O., D-Agnillo, F., Alayash, A. I. (2008) Acellular hemoglobin attenuates hypoxia-inducible factor (HIF-1alpha) and its target genes in hemodiluted rats *Biochem. J.* (In press)., Moore, E. E. (2003) Blood substitutes: The future is now *J. Am. Coll. Surg.* 196, 1-17.

Moore, E. E., Cheng, A. M., Moore, H. B. Masuno, T., Johnson, J. L. (2006) Hemoglobin-based oxygen carriers in trauma care: Scientific rationale for the US multicenter prehospital trial World J. Surg. 30, 1247-1257

Muir M. (2006) Trauma: physiology, pathophysiology, and clinical implications. *J. Vet. Emerg. Crit. Car.* 15, 253-263.

Muza S. R. (2007) Military applications of hypoxic training for high-altitude operations. *Med Sci Sport Exer,* 39, 1625-1631.

Natanson C., Kern, S. J., Luire, P. Banks, S. M. (2008) Cell-free hemoglobin-based blood substitutes and risk of myocardial infarction and death—A meta-analysis, *J Amer. Med. Assoc.* 299, 2304-2312.

Nikitin, A., Gogotsi, Y. (2004) Nanostructured carbide-derived carbon. *Encyc. Nanosci. Nanotech.* X, 1-22.

Pagona, G., Karousis, N., Tagmatarchis, N. (2008) Aryl diazonium functionalization of carbon nanohorns *Carbon* 46, 604-610.

Panessa-Warren, B. J., Warren, J. B., Wong, S. S., Misewich, J. A. (2006) Biological cellular response to carbon nanoparticle toxicity, *J. Phys-Condens. Mat.* 18, S2185-S2201.

Perakslis, E., Tuesca, A., Lowman, A. (2007) Complexation hydrogels for oral protein delivery: an in vitro assessment of the insulin transport-enhancing effects following dissolution in simulated digestive fluids *J. Biomat. Sci-Polym. E.* 18, 1475-1490.

Phillips, G. J., Lloyd, A. W., Mikhalovsky, S. V. (2006) Mesoporous carbide-derived carbon with porosity tuned for efficient adsorption of cytokines Biomaterials, 27, 5755-5762Vasseur- Reiber G. (1996) The epidemiology of diabetic foot problems *Diabetic Med.;* 13, S6-S11.

Rossen R., Kabat H., Anderson J. P. (1943) Acute arrest of cerebral circulation in man. *Arch Neurol Psychiatr.;* 50, 510-28.

Sauaia A., Moore, F. A., Moore, E. E., Moser, K. S., Brennan, R., Read, R. A. Pons, P. T. (1995) *J. Trauma* 38, 185-193

Schubert, A. (2003) Diaspirin-crosslinked hemoglobin reduces blood transfusion in noncardiac surgery: A multicenter, randomized, controlled, double-blinded trial *Anesth. Analg.* 97, 323-32.

Sellards, A. W., Minot, G. R. (1916) Injection of hemoglobin in man and its relation to blood destruction, with special reference to anemias *J. Med. Res.* 34, 469-494.

Shen, T. J, Ho, N. T., Zou, M., Sun, D. P., Cottam, P. F., Simplaceanu, V., Tam, M. F., Bell, D. A, Ho, C. (1997) Production of normal human adult and fetal hemoglobin in *Escherichia coli Protein Engineering* 10, 1085-1097.

Shen, T. J., Rogers, H., Yum X. Lin, F. Noguchi, C. T. (2007) Modification of globin gene expression by RNA targeting strategies *Exp. Hematol.* 35, 1209-1218.

Stollings, J. L., Oyen, L. J. (2006) Oxygen therapeutics: Oxygen delivery without blood. *Pharmacotherapy* 26, 1453-1464

Storz, J. F. (2007) Hemoglobin function and physiological adaptation to hypoxia in high-altitude mammals *J. Mammal.* 88, 24-31.

Strauss, M. B. (2005) Hyperbaric oxygen as an intervention for managing wound hypoxia: Its role and usefulness in diabetic foot wounds. *Foot Ankle Int.* 26, 15-18.

Tsai, C. H., Fang, T. Y., Ho, N. T., Ho, C. (2000) Novel recombinant hemoglobin ($\beta$N108Q), with low oxygen affinity, high cooperativity, and stability against autoxidation *Biochemistry* 39, 13719-13729.

Tsai, C. H., Ho, C. (2002) Recombinant hemoglobins with low oxygen affinity and high cooperativity *Biophys. Chem.* 98, 15-25.

Tsai, A. G., Cabrales, P., Manjula, B. N., Acharya, S. A., Winslow, R. M., Intaglietta, M. (2006) Dissociation of local nitric oxide concentration and vasoconstriction in the presence of cell-free hemoglobin oxygen carriers *Blood* 15, 3603-3610.

Weber, R. E. (2007) High-altitude adaptations in vertebrate hemoglobins *Respir. Physiol. Neuro.* 158, 132-142.

Weickert, M. J., Pagratis, M., Glascock, C. B., Blackmore, R. (1999) A Mutation that improves the soluble recombinant hemoglobin accumulation in *Escherichia coli* in heme excess *Appl. Environ. Microb.* 65, 640-647.

Widjaja, A. B., Tran, A., Cleland, H., Leung, M, Millar, I. (2005) The hospital costs of treating necrotizing fasciitis *ANZ J. Surg.* 75, 1059-1064

Wiltrout M. E., Giovannelli, J. L., Simplaceanu, V., Lukin, J. A., Ho, N. T., Ho, C. (2005) A biophysical investigation of recombinant hemoglobins with aromatic B10 mutations in the distal heme pockets *Biochemistry* 44, 7207-7217.

Winslow, R. M. (2003) Current status of blood substitute research: towards a new paradigm, *J. Intern. Med.* 253, 508-517.

Winslow, R. M. (2007) The role of hemoglobin oxygen affinity in oxygen transport at high altitude *Resp. physiol. Neurobi.* 128, 121-127.

Winterbourne C. C. (1990) Oxidative reactions of hemoglobin *Method. Enzymol.* 186, 265-272.

Young, M. H., Engleberg, N. C., Mulla Z. D., Aronoff, D. M. (2006) Therapies for necrotising fasciitis *Expert Opin. Biol. Th.* 6, 155-165.

Yushin, G. N., Hoffman, E. N., Nikitin, A., Ye, H. H., Barsoum, M. W., Gogotsi, Y. (2005) Synthesis of nanoporous carbide-derived carbon by chlorination of titanium silicon carbide *Carbon* 43, 2075-2082.

Yushin G, Hoffman, E. N., Barsoum, M. W., Gogotsi, Y., Howell, C. A., Sandeman, S. R., Phillips, G. J., Lloyd, A. W., Mikhalovsky, S. V. (2006a) Mesoporous carbide-derived carbon with porosity tuned for efficient adsorption of cytokines *Biomaterials,* 27:5755-5762.

Yushin, G., Dash, R., Jagiello, J., Fischer, J. E., Gogotsi, Y. (2006b) Carbide-derived carbons: Effect of pore size on hydrogen uptake and heat of adsorption *Adv. Funct. Mater.* 16, 2288-2293.

Zhu, H., Bunn, H. F. (1999) Oxygen sensing and signaling: impact on the regulation of physiologically important genes *Resp. Physiol.* 115, 239-247.

Zhu, H., Bunn, H. F. (2001) Signal transduction—how do cells sense oxygen *Science* 292, 449-451.

Zijlstra, W. G., Buursma, A., Meeuwsen-van der Roest, W. P. (1991) Absorption spectra of human feral and adult oxyhemoglobin, de-oxyhemoglobin, carboxyhemoglobin, and methemoglobin *Clin. Chem.* 37, 1633-1638.

What is claimed is:

1. An oxygen delivery system comprising carbide-derived carbon to which hemoglobin is irreversibly adsorbed, and a physiologically suitable carrier for in vivo administration.

2. The oxygen delivery system according to claim 1, additionally comprising a hydrogel coating on the carbide-derived carbon with the irreversibly adsorbed hemoglobin.

3. An oxygen delivery system according to claim 2, wherein the hydrogel coating comprises an interpenetrating network which swells and increases pore size in response to decreasing temperature.

4. An oxygen delivery system according to claim 2, wherein the hydrogel coating comprises an interpenetrating network which swells and increases pore size in response to decreasing pH.

5. The oxygen delivery system according to claim 1, wherein the hemoglobin is a mutant or a naturally occurring variant of hemoglobin having an oxygen dissociation profile which differs from that of human hemoglobin.

6. The oxygen delivery system according to claim 1, wherein the hemoglobin is a mutant or a naturally occurring variant of hemoglobin which has a higher affinity for oxygen than human hemoglobin.

7. An oxygen delivery system according to claim 1, additionally comprising an enteric coated shell which dissolves at the pH of the small intestine.

8. An oxygen delivery system according to claim 1, in the form of a powder.

9. An oxygen delivery system according to claim 1, additionally comprising a physiologically suitable carrier for parenteral administration.

10. An oxygen delivery system according to claim 1, formulated as a nebulized inhalant.

11. A method of delivering oxygen to tissues in a human subject comprising administering a formulation comprising carbide-derived carbon to which hemoglobin is irreversibly adsorbed.

12. A method according to claim 11, wherein the formulation includes an enteric coated shell which dissolves at the pH of the small intestine.

13. A method according to claim 11, wherein the formulation is a nebulized inhalant.

14. A method according to claim 11, wherein the formulation is a powder which is administered topically.

15. A method according to claim 11, wherein the formulation comprises a physiologically suitable carrier for parenteral administration.

16. An oxygen delivery system according to claim 1, wherein the carbide-derived carbon has pore size up to 500 nm.

17. An oxygen delivery system according to claim 1, wherein the carbide-derived carbon has 4 to 6 nm pores.

18. An oxygen delivery system according to claim 1, wherein the carbide-derived carbon has 0.6 to 10 nm pores.

19. An oxygen delivery system according to claim 1, comprising a mutant of hemoglobin which has an oxygen dissociation profile appropriate for treating trauma so that only trauma tissues that are hypoxic are oxygenated.

20. An oxygen delivery system according to claim 1, additionally comprising adsorbed super oxide dismutase (SOD).

21. An oxygen delivery system according to claim 20, additionally comprising adsorbed catalase (CAT).

22. An oxygen delivery system according to claim 21, additionally comprising adsorbed methemoglobin reductase (MHbR).

23. An oxygen delivery system according to claim 22, additionally comprising ascorbic acid and NADH.

24. An oxygen delivery system, consisting of:

carbide-derived carbon to which hemoglobin is irreversibly adsorbed, or carbide-derived carbon in which pore size is tuned to reversibly adsorb $O_2$.

* * * * *